US009381159B2

(12) United States Patent
Jin et al.

(10) Patent No.: US 9,381,159 B2
(45) Date of Patent: Jul. 5, 2016

(54) MICROSPHERES FOR CONTROLLED- OR SUSTAINED-RELEASE DELIVERY OF THERAPEUTICS

(71) Applicants: Tuo Jin, Shanghai (CN); Zhenhua Hu, Shanghai (CN); Weien Yuan, Shanghai (CN)

(72) Inventors: Tuo Jin, Shanghai (CN); Zhenhua Hu, Shanghai (CN); Weien Yuan, Shanghai (CN)

(73) Assignee: Tuo Jin, Shanghai (CN)

( * ) Notice: Subject to any disclaimer, the term of this patent is extended or adjusted under 35 U.S.C. 154(b) by 0 days.

(21) Appl. No.: 14/362,575

(22) PCT Filed: Dec. 5, 2012

(86) PCT No.: PCT/CN2012/085930
§ 371 (c)(1),
(2) Date: Jun. 3, 2014

(87) PCT Pub. No.: WO2013/083041
PCT Pub. Date: Jun. 13, 2013

(65) Prior Publication Data
US 2014/0314853 A1 Oct. 23, 2014

(30) Foreign Application Priority Data
Dec. 5, 2011 (CN) .......................... 2011 1 0397471

(51) Int. Cl.
| | | |
|---|---|---|
| *A61K 38/16* | (2006.01) | |
| *A61K 9/50* | (2006.01) | |
| *A61P 3/10* | (2006.01) | |
| *A61K 9/16* | (2006.01) | |
| *A61K 38/22* | (2006.01) | |
| *A61K 38/23* | (2006.01) | |
| *A61K 38/25* | (2006.01) | |
| *A61K 38/26* | (2006.01) | |
| *A61K 38/31* | (2006.01) | |

(52) U.S. Cl.
CPC ............ *A61K 9/1647* (2013.01); *A61K 9/1611* (2013.01); *A61K 9/1694* (2013.01); *A61K 38/22* (2013.01); *A61K 38/23* (2013.01); *A61K 38/25* (2013.01); *A61K 38/26* (2013.01); *A61K 38/31* (2013.01)

(58) Field of Classification Search
None
See application file for complete search history.

(56) References Cited

U.S. PATENT DOCUMENTS

| | | | |
|---|---|---|---|
| 5,912,015 A * | 6/1999 | Bernstein | A61K 9/1611 424/484 |
| 6,270,700 B1 | 8/2001 | Ignatious | |
| 2002/0045582 A1 | 4/2002 | Margolin et al. | |
| 2009/0004283 A1* | 1/2009 | Petersen | A61K 9/0019 424/490 |

FOREIGN PATENT DOCUMENTS

| | | |
|---|---|---|
| CN | 1732903 A | 2/2006 |
| CN | 101658496 A | 3/2010 |
| CN | 102488619 A | 6/2012 |
| JP | 57-118512 A | 7/1982 |
| JP | 2002-505671 A | 2/2002 |
| JP | 2011-506077 A | 3/2011 |
| WO | 02/100343 A3 | 12/2002 |
| WO | 2010/113177 A2 | 10/2010 |
| WO | WO 2010113177 A2 * | 10/2010 |

OTHER PUBLICATIONS

International Search Report, dated Mar. 14, 2013, for International Application No. PCT/CN2012/085930, 6 pages.
Written Opinion, dated Mar. 14, 2013, for International Application No. PCT/CN2012/085930, 5 pages.
Zhao et al., "Study on Preparation and in Vitro Release of 5-Fluorouracil Loaded in PLGA Sustained-Release Microspheres," *Progress in Modern Biomedicine* 11(24):4801-4803, 2011. (with English Abstract).

* cited by examiner

*Primary Examiner* — H. Sarah Park
(74) *Attorney, Agent, or Firm* — Seed IP Law Group PLLC

(57) ABSTRACT

A new microsphere formulation (composition) for controlled- or sustained-release delivery of therapeutic ingredient(s), mainly peptides and proteins not over 10K in molecular weight, comprises at least a therapeutic ingredient, a helping agent (such as PH sensitive agent whose solubility is a function of pH) and a biodegradable polymer. The therapeutic ingredient(s) and the helping agent are in the form of fine particles, less than 1O um in diameter, encapsulated in the polymer which forms the microsphere matrix. A method for preparing the composition comprises a step of in-situ precipitating the therapeutic ingredient(s) and the helping agent to the fine particles and successive steps for forming the microspheres. Such a microsphere formulation offers a well-controlled release profile for prolonged period and encapsulation efficiency over 95%.

12 Claims, 2 Drawing Sheets

MICROSPHERES FOR CONTROLLED- OR SUSTAINED-RELEASE DELIVERY OF THERAPEUTICS

CROSS REFERENCE AND RELATED APPLICATION

This application claims priority of Chinese patent application CN 201110397471.7, filed on Dec. 5, 2011. The contents of which are incorporated by reference here into this application.

FIELD OF THIS INVENTION

This invention relates a composition of sustained release dosage form of exenatide, a peptide, and a method to formulate this dosage form.

BACKGROUND OF INVENTION

The technical challenges for a polymer-based sustained-release dosage form of peptide or other water soluble ingredients comprise initial burst release, incomplete release, delayed release in the initial or any other dosing period, and degradation of the active ingredients due to acidity or generated from the polymer degradation. To ensure that the sustained-release dosage form injectable, the drug carrying polymers are often formulated to microsphere form, tens of microns in diameter, by which the active ingredients are microencapsulated. In this case, encapsulation efficiency and size control of the microspheres become a critical for therapeutically practical dosage forms. While several peptide-loaded microsphere formulations are available on the market, the above-mentioned issues have not yet been well addressed. This situation is especially true for exenatide microsphere formulation currently sold in the market, which released exenatide for a period of a week since the third week after administration. The present invention teaches microsphere composition and its formulation method for which the problems associated with microsphere formulation, especially for peptides and exenatide will be resolved.

Microspheres are formulated with a variety of reported methods, such as the solvent evaporation, coacervation, spray drying, spray freeze-drying, ultrason-assisted atomization, and microfluidization. One of the most commonly used process involves solvent evaporation or extraction after the embryonic microspheres are formed through initial emulsification of a drug-loaded polymer solution in a continuous phase which is immiscible with the polymer solution. In case that the peptides or other ingredients are in aqueous solution form, multiplexing emulsification, an emulsion is emulsified into another continuous phase is required.

Single emulsification method is only feasible for encapsulation of lipophilic ingredients which may dissolve in an organic solvent together with the polymer which offers controlled release barrier. The co-solution is then dispersed in the aqueous phase to form embryonic microspheres, followed by organic solvent removal, through evaporation or extraction, to solidify the microspheres. In most of cases, however, biologic agents such as proteins and peptides dissolves only in water, double emulsification has to be applied. If the later continuous phase is water based, the protein or peptide solution entrapped by the organic polymer droplets may leak into the aqueous continuous phase, causing reduced encapsulation efficiency. For proteins possessing susceptible conformation, the organic/water interface may be hazardous to cause protein denaturing and aggregation.

To avoid leaking of the active ingredients into the continuous phase during the microencapsulation process, non-aqueous liquids immiscible with the polymer solution, such silicone oil, are used as the later continuous phase to emulsify the drug loaded polymer solution. Since most of proteins and peptides do not dissolve in silicone oil, encapsulation efficiency may be improved substantially. The major drawback of using silicone oil, or other non-water continuous phase is to get rid of the oily material from the microspheres surfaces. Considerable amount of organic solvents miscible with silicone oil have to be used to clean the microspheres, a highly environment unfriendly process.

Another alternative to improve encapsulation efficiency is to pre-formulate the protein or peptide ingredient to solid particles prior to microencapsulation. This microsphere forming process is called "solid-in-oil-in-water" (S/O/W) method. S/O/W method will be used in the present invention wherein the process to convert the proteins or peptides to solid form is novel.

For injection convenience, the diameter of the microspheres range between few to 200 μm, preferably within 20-100 μm in most of cases. Therefore, the primary particles of proteins or peptides to be encapsulated must be substantially smaller than the microspheres of final form. It is reasonable if the diameters of the solid protein or peptide particles is adjusted to be few microns or below.

To reduce the sizes of the primary particles, some researchers precipitated polypeptides by adding water-miscible but less polar solvents into the aqueous solution of the peptides. These water miscible solvents are, however, less volatile, and difficult to be removed by evaporation. In this case, extraction becomes more efficient for solvent removal.

SUMMARY OF THE INVENTION

This invention demonstrates a composition of sustained-release microsphere dosage form which offers a nearly linear release profile of peptides for designed period of time. This invention also teaches a method for preparing this microsphere formulation. The microsphere formulation contains at least a peptide (or other active ingredient such as proteins less than 10K in molecular weight—defined as small molecular weight hereafter) and a helping agent (such as pH sensitive agents whose solubility varies as a function of pH), both are in micro-particulate form, and at least a biodegradable polymer. The pH sensitive agent (one of helping agent) helps to buffer (neutralize) the acidity generated by the polymer degradation and to accelerate drug release by adjusting osmotic pressure in the stage prior to polymer degradation and post degradation. As a method to formulate this microsphere composition (dosage form), the fine particles of the peptide and the pH sensitive agent sufficiently small in diameter (between sub-microns and few microns) are prepared by precipitation first in the solvent which dissolves the polymer. Then the formed suspension is further dispersed (emulsified) in an aqueous continuous phase to form embryonic microspheres, followed by solidification. This process may be outlined in following steps.

a) dissolving the therapeutic ingredient(s) (such as exenatide) in a polar solvent (solvent 1, such as DMSO or DMF);

b) dissolving helping agent (such as the pH sensitive agent) in water;

c) mixing the solution prepared in step a) and the solution prepared in step b) with a less polar solvent (solvent 2, such as dichloromethane, in which the biodegradable polymer may be dissolved), in arbitrary order, to precipitate the peptide and the pH sensitive agent;

d) dispersing the suspension formed in step c) into an aqueous continuous phase to form embryonic microspheres;

e) solidifying the embryonic microspheres formed in step d) by removing the organic solvent (solvent 1 and solvent 2) from the polymer phase.

The peptides or proteins of small molecular weight in the above-described composition and process comprise exenatide, other GLP-1 analogues, insulin, calcitonin, leuprorelin, triptorelin, octreotide and similar therapeutic peptides. The pH sensitive agent in the composition may be selected from $Mg(OH)_2$, $MgCO_3$, $Zn(OH)_2$ and $ZnCO_3$. The polymer used in the composition to achieve sustained- or controlled-release may be polylactic-co-glycolic acid (PLGA), polylactic acid (PLA), polycaprolactone (PCL), or poly-CBZ-pseudo-serine lactone. The polymer should well soluble in solvent 2, which precipitates the drug (such as peptides or proteins) in situ.

This microsphere (composition) design and its formulation method enable greatly increased microencapsulation (drug loading) efficiency, reduced peptide or protein degradation during prolonged sustained release period, and improved linearity of drug release profile.

DETAILED DESCRIPTION OF THE INVENTION

Design of the Composition

Figure 1:
FIG. 1 Morphology of in-situ particles of exenatide and exenatide loaded microspheres FIG. 2 Cumulative exenatide release profile, release media: PBS (pH 7.4) with different $Mg(OH)_2$ content: (0.0% ♦; 6.06% ▲; 8.82% ●; 11.43% ■)

This invention referred to an improved microsphere formulation for peptides and proteins, as well as a microencapsulation process, called solid-in-oil-in-water (S/O/W), to prepare the microsphere formulation (the composition). The improvement in composition and method involves forming fine particles of the peptides (or proteins having no conformational instability issues) and/or the pH sensitive agent through their precipitation in the solvent (solvent 2 mentioned above) in which the polymer may be dissolved. To ensure satisfied encapsulation efficiency and release kinetics, the particle diameter of the precipitates should be below 10 μm and best to be around 1 μm.

Working Mechanism

Since solidification of peptides (or proteins) greatly reduced its dissolution rate in the hydrophobic polymer matrix where only limited water penetrate into during the S/O/W process of microencapsulation, the chance for the peptide (or protein) to leak to the aqueous continuous phase can be retarded.

During sustained-release in vivo (or in vitro), the matrix of microspheres formed of biodegradable polymer (such as PLGA) absorbs body fluid (or water) and slightly swells after injection. At the stage when only limited body fluid (or water) penetrates into the polymer matrix, the pH sensitive agent quickly dissolves and generates sufficient osmotic pressure to accelerate swelling of the polymer, thus accelerating the peptide release. When more water (or body fluid) enters the polymer matrix, the pH sensitive agent has reached its solubility and no longer to increase osmotic pressure further. At the later stage when a sustained-release rate reduced normally, the pH sensitive agent increases its solubility due to the acidic environment created by the polymer (such as PLGA) degradation.

To ensure the working mechanism of the microsphere (composition) design, the particle sizes of the peptide (or protein or other active ingredient) and the pH sensitive agent must be small enough. A general rule for the sizes of the inner particles (particles being encapsulated in another particle, say a microsphere) should be no larger than 5% of that of the microsphere (in which they are encapsulated). To achieve such small and relatively uniform inner particles of the drug and the helping agent (such as the pH sensitive agent), an in situ precipitation step is incorporated in the preparation process (the method). The pH sensitive agent in the composition may be selected from $Mg(OH)_2$, $MgCO_3$, $Zn(OH)_2$ and $ZnCO_3$. The in situ precipitation, on another hand, is achieved by mixing "good" and "bad" solvents of the peptides (or proteins and other drugs) and the helping agent (such as pH sensitive agent). The operation procedure involves dissolving the drug and the agent in their good solvent, and mixing the solution formed with good solvent with their bad solvent to enforce a precipitation. The bad solvent, however, should be a good solvent for the biodegradable polymer which plays the major role for controlled sustained release. The polymer used in the composition to achieve sustained- or controlled-release may be polylactic-co-glycolic acid (PLGA), polylactic acid (PLA), polycaprolactone (PCL), or poly-CBZ-pseudo-serine lactone. The polymer should well soluble in solvent 2, which precipitates the drug (such as peptides or proteins) in situ.

Preparation Procedure

As long as the working mechanism has been understood, the operation procedure becomes straightforward. The basic steps will be the same as those listed in "Summary of the Invention". To offer readers an easy comprehensibility, we relist the steps below.

a) dissolving the therapeutic ingredient(s) (such as exenatide) in a polar solvent (solvent 1, such as DMSO or DMF);

b) dissolving the helping agent (such as pH sensitive agent with solubility varying as a function of pH) in water;

c) mixing the solution prepared in step a) and the solution prepared in step b) with a less polar solvent (solvent 2, such as dichloromethane, in which the biodegradable polymer may be dissolved), in arbitrary order, to precipitate the peptide and the pH sensitive agent;

d) dispersing the suspension formed in step c) into an aqueous continuous phase to form embryonic microspheres;

e) solidifying the embryonic microspheres formed in step d) by removing the organic solvent (solvent 1 and solvent 2) from the polymer phase.

For the order in mixing solvent 1 (wherein the peptide or protein is dissolved) and solvent 2, or mixing the aqueous solution of the helping agent (such as the pH sensitive agent), the operator may chose any of them from those, 1) adding the peptide (or protein) solution into solvent 2; 2) adding solvent 2 into the peptide solution; 3) adding the aqueous solution of the pH sensitive agent into solvent 2; 4) adding solvent 2 into the aqueous solution of the pH sensitive; or mixing all of them together. The pH sensitive agent in the composition may be selected from $Mg(OH)_2$, $MgCO_3$, $Zn(OH)_2$ and $ZnCO_3$.

Once the fine particle-in-polymer solution system is prepared, the particle-in-oil phase may be subjected to any of the microsphere forming process reported in the literature such as S/O/W, spray drying, or spray freeze-drying (in cold liquid such as liquid nitrogen).

In case the polar solvent for dissolving peptide is less volatile, extraction should be chosen to remove the solvents from the microspheres formed.

To ensure that fine particles of the drug and hydrophilic helping agent to uniformly distributed in solid-in-oil suspension, surfactant may need to be added in the aqueous solution of the agent. The surfactant is selected from but not limited to: oleic acid sodium, sodium stearate, twelve sodium alkyl sulfonate, polyvinyl alcohol, sodium carboxymethyl cellulose, lecithin, gelatin, hyaluronic acid, Twain or their mixture.

This patent application used Exenatide (Exendin-4) as one example to demonstrate the composition and the method. Exenatide is the United States southwest of the Gila monster when eating secreted a polypeptide containing 39 amino acids in saliva. Exendin-4 is glucagon-like peptide 1 (GLP-1) analogues, and its homology with mammalian GLP-1 amino acid sequence is 53%, and is a valid GLP-1 receptor agonist. Exendin-4 can control blood glucose concentration relying on glucose and stimulate insulin secretion and inhibit glucagon secretion and inhibit pancreatic islet B cell apoptosis and slow gastric emptying and reduce appetite and have other physiological activity, which is suitable for the treatment of type2 diabetes. These physiological activities of Exendin-4 are similar to that of GLP-1, but GLP-1 in vivo was rapidly degraded by two peptide peptidase IV (DPPIV). The half-life of GLP-1 is only 1-2 minutes, it will soon be cleared, but Exendin-4 is not easy to be degraded by DPPIV due to it has certain resistance effect, so circulating in vivo is longer can be up to 60-90 minutes. Therefore, Exenatide is considered the next generation of ideal therapeutic drugs for type II diabetes.

Since all the peptides and small proteins (those have no conformational stability issues) have highly similar molecular structure and physical chemical properties, the solvents and formulation procedure used for exenatide in the examples of the disclosure will apply perfectly for all the peptides and small proteins. Therefore, the examples should be used to understand this invention but not limit the right of this invention.

As a representative of non-limiting example, polymer may comprise polylactic acid or polyglycolic acid copolymer, or blends thereof. Preferably, the polymer to the concentration of 5%-25% W/V dissolved in weakly polar solvent B2, more preferably, for 7.5%-25% W/V.

Examples

The polymers used in the examples are polylactic-co-polyglycolic acid (PLGA, lactide:glycolide=50:50, 14-16K in molecular weight, and 0.39 in intrinsic viscosity).

Improved S/O/W Microencapsulation Method

An in-situ S/O/W emulsion solvent evaporation was used to prepare exenatide microspheres. DMSO solution of exenatide and proper amount of $Mg(OH)_2$ were added into 2 ml DMC containing 100 mg PLGA and mixed to form in-situ S/O emulsion. The primeval emulsion was poured to aqueous phase (1% PVA solution) to form S/O/W emulsion. The solvent evaporation at room temperature was carried out at 250 rpm for 4 h. Microspheres were collected by centrifuged and washed with distilled water for three times.

Analysis of Drug Loading and Encapsulation Efficiency

Lyophilized PLGA microspheres (10-15 mg) were dissolved with 0.5 ml DCM. After violent agitation, the suspension was centrifuged (5000 rpm, 5 min) and 200 ul supernatant was extracted for HPLC analysis (Agilent 1000, Agilent Technologies, USA). The HPLC analysis was conducted with C-18 RP column, 0.1% (v/v) TFA as buffer A, 0.1% (v/v) TFA+80% (v/v) acetonitrile as buffer B and the elution gradient being 60-40B % 40 min. The quantity of exenatide was evaluated by UV absorption at 280 nm. Drug loading was determined as: percent drug loading=(weight of drug entrapped/weight of microspheres used)×100. The encapsulation efficiency was determined as: (experimental drug loading/theoretical drug loading)×100. It can be seen from Table 1 that encapsulation efficiency (EE) of all the formulations were above 90%.

TABLE 1

Encapsulation efficiency of exenatide loaded microspheres with different $Mg(OH)_2$ contents. Data shown as mean ± S.D

| Formulation | $Mg(OH)_2$ content (%) | Loading capacity (%) | Encapsulation efficiency (%) |
| --- | --- | --- | --- |
| 1 | 0 | 3.13 ± 0.03 | 97.01 ± 1.77 |
| 2 | 6.06% | 2.93 ± 0.03 | 96.60 ± 1.43 |
| 3 | 8.82% | 2.81 ± 0.01 | 95.49 ± 1.15 |
| 4 | 11.43% | 2.71 ± 0.01 | 94.90 ± 0.65 |

Microsphere Morphology and Particle Size Distribution

The diameter and surface morphology of PLA microcapsules and particles were observed by a JSM-6700F (JEOL, Japan) scanning electron microscope (SEM). The specimens for SEM observation were prepared by mounting sample on metal stubs with double-sided conductive adhesive tape and coating a thin gold film (approx. 60 nm in thickness) on sample under a reduced pressure below 5 Pa with a JFC-1600 fine coater (JEOL, Japan). As shown in FIG. 1, fine particles of exenatide with average sizes less than 200 nm were in favour of encapsulation into microspheres. FIG. 1 showed the SEM photographs of exenatide loaded microspheres prepared by in-situ S/O/W SPG membrane emulsification technique. The microspheres exhibited a spherical shape and smooth surface. The diameter of microspheres is around 60 μm and exhibited a narrow size distribution.

Microspheres in Vitro Release Test

Figure 2:
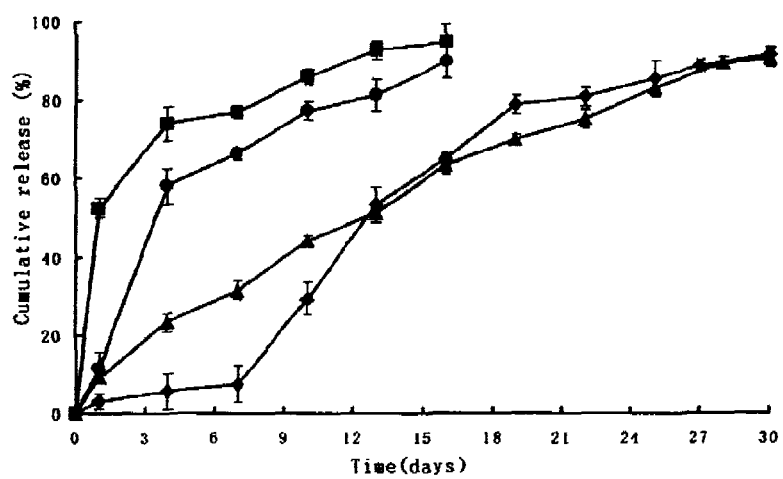

PLGA microspheres (20-30 mg) were placed in an Eppendorf tube and 1 ml PBS (pH=7.4) was added. The mixture was gently agitated (100 rpm) at 37° C. At certain intervals, the mixture was centrifuged and 100 ul supernatant was used to analyze the released exenatide with HPLC (Agilent 1100, Agilent Technologies, USA). Then 100 ul fresh buffer was added into the remaining mixture to keep the whole volume constant. After that, the mixture was violently agitated to re-suspend the microspheres. The suspension was then gently agitated (100 rpm) at 37° C. The in vitro release profiles of exenatide from PLGA microspheres with different contents of $Mg(OH)_2$ investigated and shown in FIG. 2. The cumulative release of microsphere without $Mg(OH)_2$ is less than 20% over 7 days, while, the initial cumulative releases over 7 days of microspheres with 11.43% $Mg(OH)_2$ was 77%, with 8.82% $Mg(OH)_2$ was 66.33% and with 11.43% $Mg(OH)_2$ was 44.03%. The reason that $Mg(OH)_2$ sharply increased the initial release rate of microspheres as we expected was that the osmotic pressure created by $Mg(OH)_2$ derived water fast diffuse into microspheres. At this initial period, drug release rate from PLGA was mainly controlled by diffusion rate of water into microspheres. Subsequently, a fast release phase appeared in microspheres without $Mg(OH)_2$, of which the release percent was about 60% from 7th day to 16th day. While, the release amount of microspheres with $Mg(OH)_2$ were only about 30%. During this period, PLGA polymer started to degrade and produce acidic monomer which could accelerate degradation rate of PLGA polymer. At this period, drug release rate was mainly controlled by degradation rate of PLGA polymer. In microspheres with $Mg(OH)_2$, the acidic monomer maybe be neutralized so that degradation rate of PLGA polymer got slower than microspheres without $Mg(OH)_2$. Finally, the cumulative release of all the formulations achieved completed release over 30 days release. The release profile of microspheres with 6.06% $Mg(OH)_2$ seemed to appear a near zero-order kinetics release over the whole release period.

Efficacy of Exenatide Microspheres in c57 Mice

Figure 3:
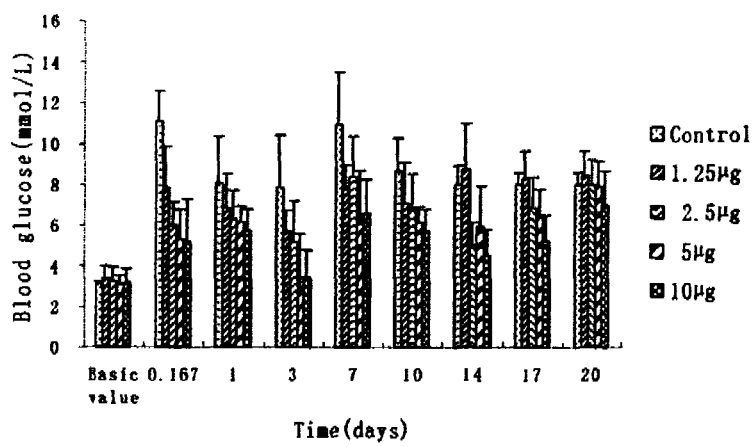
FIG. 3 The blood glucose concentrations of c57 mouse before and after SC administration of microspheres at exenatide dose of 1.25 μg/20 g, 2.5 μg/20 g, 5 μg/20 g and 10 μg/20 g FIG. 4 Average plasma drug concentration-time profiles following SC injection of exenatide-loaded microspheres in SD rats (♦) and blank microspheres (▲)

The efficacy of exenatide was assessed in male C57 mouse, which were randomly assigned to six groups respectively treated with exenatide solution, four dosages of exenatide microspheres and saline vehicle. At predetermined time intervals, a glycemic load was given to every mouse after fasting for 12 h and fasting blood glucose were measured as basic blood glucose every time. Glycemic load is to say that 20% glucose solutions were administrated into every mouse according to 0.2 ml per 20 g. After injecting glucose solution for 30 min, blood glucose concentrations of every mouse were measured again. The changes of blood glucose relative to the basic blood glucose were used to estimate the efficacy of exenatide microspheres. The blood glucose concentrations of blood samples collected from the tail vein were determined by glucose oxidase method. All groups of mouse were fasting at 5:00 PM and received a glycemic load at 9:00 AM next day after measurement of fasting blood glucose. Exenatide solution-treated group received subcutaneous (SC) injections of exenatide solution at a dose of 0.025 µg/20 g before giving every time glycemic load. The exenatide microspheres-treated groups respectively received a single SC injection of exenatide microspheres at dose of 6.25 µg/20 g, 12.5 µg/20 g, 25 µg/20 g and 50 µg/20 g. The aqueous vehicle-treated group received a single injection of the saline vehicle at a volume of 0.2 ml/20 g. To estimate effectiveness of exenatide microspheres prepared by this method, the formulation of exenatide microspheres with 6.06% $Mg(OH)_2$ was chosen to be injected into c57 mouse. As shown in FIG. 3, there was no significant difference of fasting glucose concentrations (Basic value) in every group of mouse before administration of drug. After glycemic load to each group, blood glucose concentrations of groups of microspheres were significantly lower than control group over 10 days. For groups of microspheres with exenatide dose of 2.5 µg, 5 µg, the effect can sustain for 17 days. When dosage of exenatide increased to 10 µg/20 g, efficacy of regulating blood sugar level can last for 20 days.

Plasma Concentrations of Exenatide in SD Rats

Figure 4:
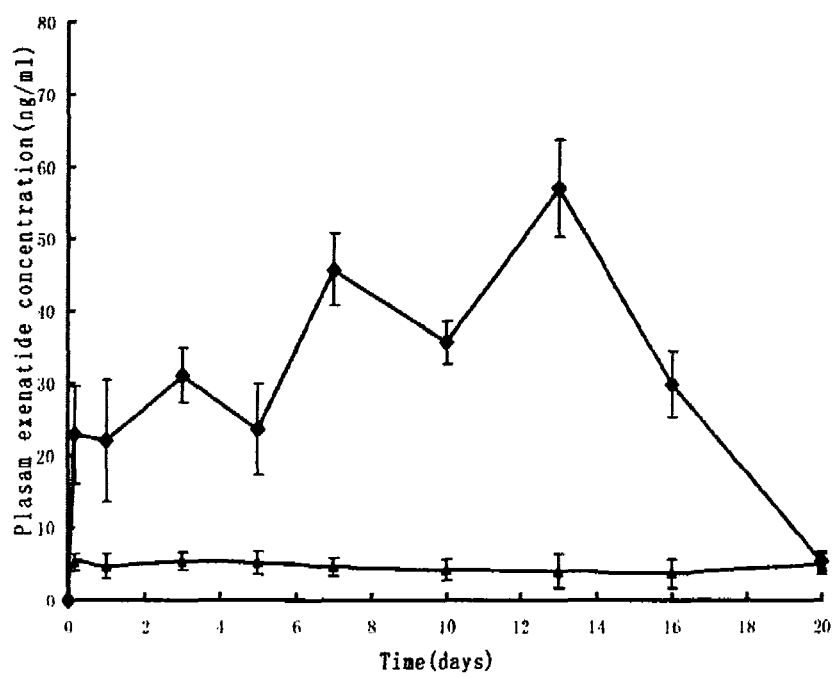

Exenatide pharmacokinetics was assessed in male SD rats. The rats received a single SC injection of an aqueous suspension of CMC-Na and Mannitol at an exenatide dose of 2 mg/ml/kg. The homogeneous dispersion was prepared within 2 min by suspending the microspheres in an aqueous vehicle. Blood samples were collected from the tail vein into tubes containing heparin sodium at the following time points: before exenatide injection; 4 h post-injection and 1, 3, 5, 7, 10, 13, 16, 20 days post-injection. After centrifugation (5000 g, 10 min), plasma was collected and stored at −20° C. until it could be analyzed for exenatide. Plasma concentrations of exenatide were measured using the Exendin-4 EIA kit (EK-070-94, Phoenix pharmaceuticals, Calif., USA). The exenatide standard provided in the ELISA kit was serially diluted using 10% rat plasma to minimize plasma interference. As shown in FIG. 4, in SD rats treated with exenatide microspheres with 6.06% $Mg(OH)_2$ at an exenatide dose of 2 mg/kg, plasma exenatide concentrations increased rapidly, reaching 22.7 ng/ml within four hours. Following with that the plasma exenatide concentration kept above 22.7 ng/ml until the 16th day. At the 13th day there is a Cmax amounts to 57.1 ng/ml, which is not more three times than the average concentration of 22.7 ng/ml.

The invention claimed is:

1. A composition comprising a plurality of microspheres, each microsphere comprising:
    a) a biodegradable polymer forming a matrix of the microsphere;
    b) a particulate GLP-1 receptor agonist distributed in the matrix of the microsphere; and
    c) a particulate helping agent selected from $Mg(OH)_2$, $MgCO_3$, and $Zn(OH)_2$ distributed in the matrix of the microsphere, wherein the particulate helping agent is less than 8.82 w/w % of the total mass of the microsphere wherein the particulate GLP-1 receptor agonist and the particulate helping agent are less than 10 µm in size and are encapsulated by the biodegradable polymer; and wherein the GLP-1 receptor agonist is exenatide.

2. The composition of claim 1, wherein the biodegradable polymer is polylactic-co-glycolic acid (PLGA), polylactic acid (PLA), or polycaprolactone (PCL).

3. The composition of claim 1 wherein the particulate GLP-1 receptor agonist and the particulate helping agent of $Mg(OH)_2$, $MgCO_3$, or $Zn(OH)_2$ are around 1 µm in size.

4. A method to prepare the composition of claim 1, comprising,
    a) suspending the particulate GLP-1 receptor agonist and particulate $Mg(OH)_2$, $MgCO_3$, or $Zn(OH)_2$ in an organic solution having the biodegradable polymer and an organic solvent;
    b) dispersing the suspension made in step a) into an aqueous continuous phase to form embryonic microspheres;
    c) removing the organic solvent of the embryonic microspheres made in step b) to solidify them.

5. The method of claim 4, wherein the particulate GLP-1 receptor agonist and the particulate $Mg(OH)_2$, $MgCO_3$, or $Zn(OH)_2$ are around 1 µm in size.

6. The method of claim 4, in case the particulate GLP-1 receptor agonist or the particulate $Mg(OH)_2$, $MgCO_3$, or $Zn(OH)_2$ helping agent are over 10 µm in size, the method further comprising in situ precipitation to reduce the particle sizes by:
    a) dissolving the particulate GLP-1 receptor agonist in a polar solvent,
    b) dissolving $Mg(OH)_2$, $MgCO_3$, or $Zn(OH)_2$ in a small amount water; and
    c) mixing the solutions of steps a) or b) into the organic solution of the biodegradable polymer to precipitate the therapeutic ingredient or $Mg(OH)_2$, $MgCO_3$, or $Zn(OH)_2$ to particles less than 10 µm in size.

7. The method of claim 6, wherein the solutions made in steps a) or b) are mixed into the organic solution of the biodegradable polymer at step c) to precipitate the particulate GLP-1 receptor agonist or $Mg(OH)_2$, $MgCO_3$, or $Zn(OH)_2$ to particles not over 1 µm in size.

8. The method of claim 6, wherein the polar solvent is selected from DMSO and DMF.

9. The method of claim 6, wherein the organic solvent in the organic solution of the biodegradable polymer is selected from dichloromethane and ethyl acetate.

10. The method of claim 4, wherein the biodegradable polymer is selected from polylactic acid (PLA), polylactic-co-glycolic acid (PLGA), or polycaprolactone (PCL).

11. The method of claim 4, wherein the aqueous continuous phase further includes polyvinyl alcohol as a surfactant.

12. The composition of claim 1, wherein the content of the helping agent is less than 6.06 w/w % in the total mass of the microspheres.

* * * * *